(12) United States Patent
Bourlion et al.

(10) Patent No.: US 11,291,381 B2
(45) Date of Patent: Apr. 5, 2022

(54) MEDICAL SYSTEM

(71) Applicant: SPINEGUARD, Vincennes (FR)

(72) Inventors: Maurice Bourlion, Rive de Gler (FR); Ciaran Bolger, Dublin (IE); Olivier Frezal, Rosny Sous Bois (FR); Stéphane Bette, Corte Madera, CA (US)

(73) Assignee: SPINEGUARD, Vincennes (FR)

( * ) Notice: Subject to any disclaimer, the term of this patent is extended or adjusted under 35 U.S.C. 154(b) by 401 days.

(21) Appl. No.: 15/565,015

(22) PCT Filed: Apr. 6, 2016

(86) PCT No.: PCT/FR2016/050789
§ 371 (c)(1),
(2) Date: Oct. 6, 2017

(87) PCT Pub. No.: WO2016/162634
PCT Pub. Date: Oct. 13, 2016

(65) Prior Publication Data
US 2018/0098714 A1    Apr. 12, 2018

(30) Foreign Application Priority Data
Apr. 7, 2015 (FR) .................. 15 52988

(51) Int. Cl.
*A61B 17/00* (2006.01)
*A61B 5/00* (2006.01)
(Continued)

(52) U.S. Cl.
CPC .......... *A61B 5/0538* (2013.01); *A61B 5/0537* (2013.01); *A61B 5/4504* (2013.01);
(Continued)

(58) Field of Classification Search
CPC ......... A61B 5/05; A61B 5/053; A61B 5/0531; A61B 5/063; A61B 5/746;
(Continued)

(56) References Cited

U.S. PATENT DOCUMENTS 5,902,105 A    5/1999 Uejima et al.
6,337,994 B1 *  1/2002 Stoianovici ............ A61B 5/053
433/27

(Continued)

FOREIGN PATENT DOCUMENTS

FR      2 865 922 A1    8/2005
WO    WO 2012/066231 A1    5/2012

OTHER PUBLICATIONS

Haas, E. C., & Edworthy, J. (1996). Designing urgency into auditory warnings using pitch, speed and loudness. Computing & Control Engineering Journal, 7(4), 193-198. (Year: 1996).*

(Continued)

*Primary Examiner* — Devin B Henson
*Assistant Examiner* — H. Q. Nguyen
(74) *Attorney, Agent, or Firm* — von Briesen & Roper, s.c.

(57) ABSTRACT

A medical system including a body; a first electrode; a second electrode; an electric generator; and a processing device suitable for determining an electrical characteristic that represents the capacity of the tissue of an anatomical structure between first and second contact surfaces of the first and second electrodes to conduct the electric current, and for emitting a warning signal corresponding to the determined electrical characteristic, the warning signal being intermittent. The processing device is suitable for detecting a variation in the electrical characteristic and for varying at least one variable parameter of the warning signal (Continued)

after a time delay, in accordance with the variation in the electrical characteristic, has elapsed.

16 Claims, 6 Drawing Sheets

(51) Int. Cl.
    *A61B 17/16*     (2006.01)
    *A61B 5/0538*     (2021.01)
    *A61B 5/0537*     (2021.01)
    *A61B 34/00*     (2016.01)

(52) U.S. Cl.
    CPC ........ *A61B 5/4566* (2013.01); *A61B 17/1626* (2013.01); *A61B 17/1671* (2013.01); *A61B 5/417* (2013.01); *A61B 34/76* (2016.02); *A61B 2017/00119* (2013.01)

(58) Field of Classification Search
    CPC ........... A61B 2017/00119; A61B 2090/08021; A61B 17/1671; A61B 5/4566; G08B 21/0244; G08B 21/0247; G08B 21/025
    See application file for complete search history.

(56) References Cited

U.S. PATENT DOCUMENTS

| | | | |
|---|---|---|---|
| 7,580,743 B2 * | 8/2009 | Bourlion | A61B 5/053 600/547 |
| 9,095,316 B2 * | 8/2015 | Welch | A61B 5/746 |
| 9,538,935 B2 * | 1/2017 | Bourlion | A61B 5/6878 |
| 9,901,283 B2 * | 2/2018 | Bourlion | A61B 5/4504 |
| 2005/0119660 A1 | 6/2005 | Bourlion et al. | |
| 2007/0153985 A1 * | 7/2007 | Tsao | G08B 17/00 379/37 |
| 2008/0067263 A1 * | 3/2008 | Modlin | A01M 1/245 239/70 |
| 2008/0175299 A1 * | 7/2008 | Mahajan | A61B 5/01 374/44 |
| 2008/0269645 A1 * | 10/2008 | Bourlion | A61B 5/053 600/594 |
| 2010/0016682 A1 * | 1/2010 | Schluess | A61B 5/08 600/301 |
| 2013/0226025 A1 | 8/2013 | Bourlion et al. | |

OTHER PUBLICATIONS

International Search Report related to Application No. PCT/FR2016/050789 dated Jun. 21, 2016.

\* cited by examiner

MEDICAL SYSTEM

CROSS-REFERENCE TO RELATED APPLICATION

This Application is a 35 USC § 371 US National Stage filing of International Application No. PCT/FR2016/050789 filed on Apr. 6, 2016, and claims priority under the Paris Convention to French Patent Application No. 15 52988 filed on Apr. 7, 2015.

FIELD OF THE DISCLOSURE

The invention relates to a medical system.

In particular, the invention relates to a medical system intended for penetrating an anatomical structure of a patient, said anatomical structure having tissues presenting different capacities for conducting an electric current. The medical system is of a type comprising:
- a body suitable for penetrating the anatomical structure, the body having an outer surface,
- at least one first electrode having a first contact surface arranged on the outer surface of the body so as to come into contact with the tissues of the anatomical structure,
- at least one second electrode having a second contact surface arranged on the outer surface of the body so as to come into contact with the tissues of the anatomical structure at a distance from the first contact surface,
- an electric generator suitable for applying an electric current between the first and second contact surfaces,
- a processing device suitable for determining an electrical characteristic representative of the capacity of the tissue of the anatomical structure between the first and second contact surfaces to conduct the electric current, and for emitting a warning signal corresponding to the determined electrical characteristic, the warning signal having at least one parameter that varies as a function of the determined electrical characteristic.

BACKGROUND OF THE DISCLOSURE

Patent application WO 03/068076 discloses a medical system of the aforementioned type, in the form of a surgical instrument in which the warning signal is intermittent and has a warning cadence at which user-perceptible warning sections are successively emitted with a time interval between two successive warning sections.

This surgical instrument, sold under the name Pedi-Guard®, is especially used in orthopedic surgery to ensure proper positioning of pedicle screws in the vertebral pedicles of a patient's vertebra for the attachment of a prosthesis or an implant. Indeed, it is important to ensure accurate positioning of pedicle screws in the spongious bone of the vertebral pedicles in order to anchor the prosthesis or implant in a satisfactory manner without damaging or even worse traversing the layer of internal cortical bone bordering the vertebral foramen through which the spinal cord passes or the layer of external cortical bone adjacent to the nerve roots. Variations in the warning signal provide information on the tissue adjacent to the first and second contact surfaces: cortical bone has a lower electrical conductivity than spongious bone which in turn has a lower electrical conductivity than fluids, such as blood, or soft tissue.

This surgical instrument, which is simple and intuitive to use, is entirely satisfactory and offers spectacular success rates for the placement of pedicle screws.

However, in certain specific situations, particularly when the tissues encountered have numerous local inhomogeneities, the sensitivity of the surgical instrument to localized changes in the capacity to conduct electric current can lead to difficulties in interpreting the warning signal. In particular, these localized changes can result in unwanted variations in the warning signal which interrupt the succession of warning sections and time intervals expected by the practitioner. The occurrence of numerous variations in the capacity to conduct electric current, within a short period of time, can also lead to artifacts in the warning signal, providing the practitioner with information that is unfamiliar or difficult to interpret.

In these particular circumstances, proper use of the surgical instrument may rely on the experience of the practitioner in distinguishing the information to be taken into account.

SUMMARY OF THE DISCLOSURE

The invention aims to overcome this problem by improving the reliability of the medical system, regardless of its use.

To this end, the invention provides a medical system of the aforementioned type wherein the processing device is suitable for detecting a variation of the electrical characteristic and for varying said at least one variable parameter of the warning signal after a time delay following the variation of the electrical characteristic has elapsed.

Thus, the invention provides that a period defined by the time delay precedes the emitting of the warning signal with the parameter(s) corresponding to the determined electrical characteristic. The emitting of the warning signal with the parameter(s) corresponding to the determined electrical characteristic is therefore delayed relative to the detection of the variation in the electrical characteristic. The time delay thus enables limiting or adjusting the sensitivity of the medical system to localized changes in the capacity to conduct electric current of the tissues encountered. This reduces unwanted variations in the warning signal and the risk of artifacts, thereby improving the reliability of the medical system.

The time delay may be equal to at least a portion of a warning period corresponding to the warning cadence, in particular equal to at least a portion of the time interval, preferably between 30% and 100% of the time interval, particularly between 50% and 100%, for example between 60% and 90%.

According to an alternative, the processing device may determine the electrical characteristic at a measurement frequency, the electric current having a measurement period corresponding to the measurement frequency, and the time delay may be equal to at least a portion of the measurement period, preferably between 10% and 500% of the measurement period.

The time delay may be greater than two times the measurement period, and the processing device may be adapted to calculate an average electrical characteristic from electrical characteristics determined at each of the measurement periods occurring during the time delay, and to vary the warning signal parameter as a function of the calculated average electrical characteristic.

The measurement period may be between 50 ms and 250 ms, preferably 200 ms.

Said at least one variable parameter of the warning signal may include the warning cadence, the processing device being adapted to modify the warning cadence after the time delay has elapsed.

The warning cadence may be between 1 Hz and 20 Hz.

Said at least one variable parameter of the warning signal may include a warning frequency at which each of the warning sections is emitted, the processing device being adapted to change the warning frequency after the time delay has elapsed.

The warning frequency may be between 470 Hz and 2600 Hz.

Said at least one variable parameter of the warning signal may include a warning amplitude, the processing device being adapted to modify the warning amplitude after the time delay has elapsed.

The processing device may be adapted to determine an electrical conductivity as an electrical characteristic, and to:
increase the warning signal parameter when the electrical conductivity increases,
decrease the warning signal parameter when the electrical conductivity decreases.

Alternatively, the processing device may be adapted to determine an electrical resistivity as an electrical characteristic, and to:
increase the warning signal parameter when the electrical resistivity decreases,
decrease the warning signal parameter when the electrical resistivity increases.

The processing device may be adapted to keep constant said at least one variable parameter of the warning signal as long as the electrical characteristic is below a threshold, and to vary the parameter of the warning signal when the electrical characteristic reaches the threshold.

BRIEF DESCRIPTION OF THE DRAWINGS

Other objects and advantages of the invention will be apparent from the following description of a particular embodiment of the invention, given by way of non-limiting example, the description being made with reference to the accompanying drawings.

DETAILED DESCRIPTION OF THE DISCLOSURE

In the figures, the same references designate identical or similar elements.

Figure 1:
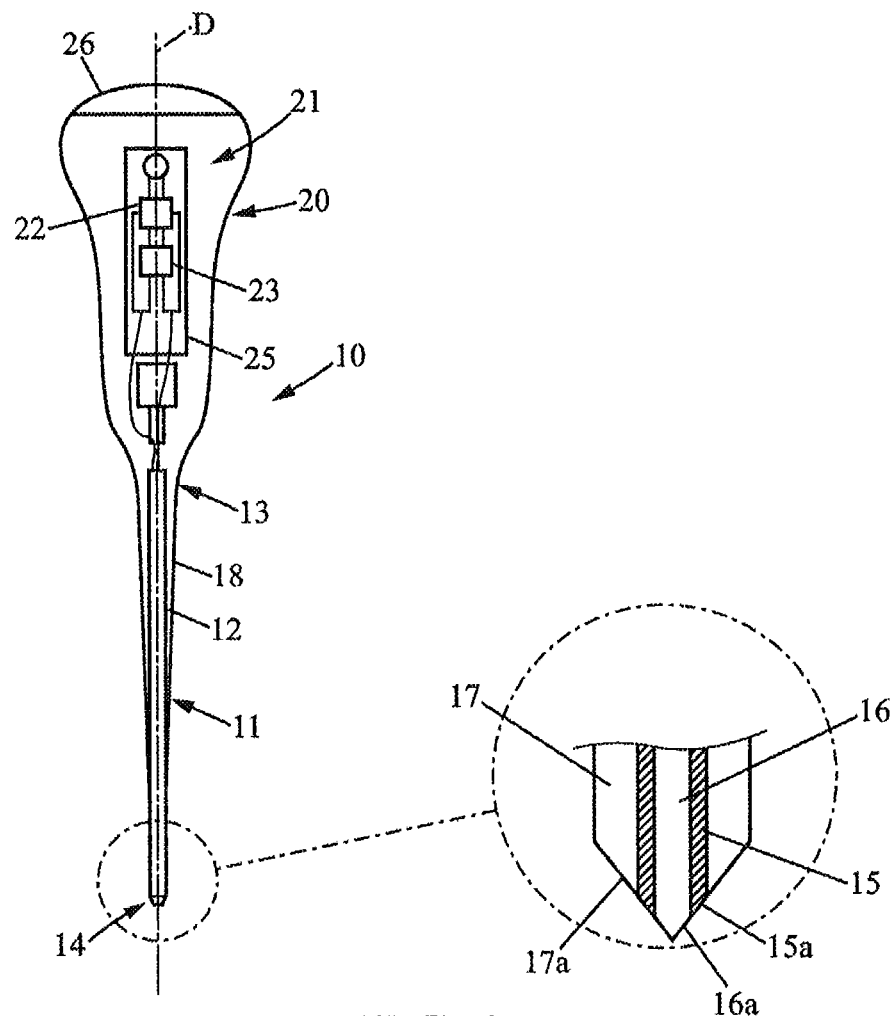
FIG. 1 is a schematic representation of a medical system according to an embodiment of the invention, the medical system comprising a processing device suitable for emitting a warning signal corresponding to an electrical characteristic representative of the capacity of a tissue of an anatomical structure to conduct an electric current between first and second contact surfaces.

FIG. 1 schematically represents a medical system in the form of a surgical instrument 10 which can be manually manipulated by a practitioner in order to drill into a bone structure 3, such as a vertebra 2 of the spinal column of a patient. However, the invention is not limited to this type of surgical instrument nor to an application in a bone structure. In particular, the invention can be implemented for any type of anatomical structure with any type of medical system manipulated manually or by means of a robotic arm. The medical system may comprise any type of instrument or tool for surgical or medical use, manual or motorized, and in particular a probe, an awl, a burr, a spatula, or a curette. It may also include an implant such as a screw, and in particular a pedicle screw.

The tool 10 comprises a body 11 adapted to penetrate the bone structure 3, and a housing 20 forming a handle integrally secured to the body 11 and adapted to be held by the hand of the practitioner. Depending on the application, the housing 20 may also be adapted to be integrally secured to an end of a robotic arm.

The body 11 has an outer surface 12 and serves to support first 16 and second 17 electrodes respectively having first 16a and second 17a contact surfaces arranged to come into contact with the bone structure 3 at a distance from each other.

In the embodiment shown, the body 11 is conical having a circular cross-section along a central axis D and extends from a proximal end 13 integrally secured, optionally detachably, to the handle 20, to a distal end 14 defining an end of penetration, frustoconical or pyramidal. The body 11 could, however, have any other shape, including conical or cylindrical with polygonal cross-section or other shape.

The first electrode 16, cylindrical and made of conductive material, extends inside the body 11 parallel to the central axis D. In particular, the first electrode 16 is arranged in a central bore of the body 11 and extends coaxially to the central axis D to a free end forming the first contact surface 16a. The first contact surface 16a is flush with the outer surface 12 of the body 11 at its distal end 14.

The second electrode 17, annular and made of conductive material, extends along the central axis D around the first electrode 16. The second electrode 17 may, in particular, be formed by the body 11 itself, which is then made of a conductive material. The second contact surface 17a of the second electrode 17 is composed of a cylindrical portion parallel to the central axis D corresponding to a side surface of the body 11, and an annular portion transverse to the central axis D corresponding to a distal surface of the body 11.

A layer of electrically insulating material 15 is interposed between the first 16 and second 17 electrodes. The layer of electrically insulating material 15 extends along the body 11 from the proximal end 13 of the body 11 to the distal end 14 of the body 11 with which its free end surface 15a is flush. In the embodiment shown, the layer of electrically insulating material 15, annular, extends along the central axis D around the first electrode 16 and inside the second electrode 17.

However, the invention is not limited to the embodiment and arrangement described above for the body 11, the first 16 and second 17 electrodes, and the layer of electrically insulating material 15. More generally, the first 16 and second 17 electrodes are not necessarily arranged coaxially. In particular, these first 16 and second 17 electrodes may each be implemented as a rod of conductive material inserted into the body 11. Furthermore, the first electrode 16 and second electrode 17 may each have an isolated contact surface 16a, 17a flush with the side surface or the distal surface of the body 11. In addition, the body 11 may support two or more than two first electrodes 16 and two or more than two second electrodes 17.

The handle 20, a rotationally symmetrical cylinder, extends substantially coaxially to the central axis D of the body 11. The handle 20 has a form which facilitates gripping and handling the tool 10. The handle 20, made of plastic, is integral with a plastic sleeve 18 extending over a portion of the outer surface 12 of the body 11.

The handle 20 comprises a housing 21 adapted to receive an electric generator 22 and a processing device 23, for example, placed on a circuit board 25 inserted into the housing 21 through an opening provided at an end of the handle 20 that is opposite to the body 11. A removable cover 26 is used to close the housing 21.

The electric generator 22 is adapted to apply an electric current M between the first 16a and second 17a contact surfaces. In one particular embodiment represented in FIG. 3, but not limited thereto, the electric generator generates the electric current M in the form of pulses of 1.2 V at a measurement frequency of 5 Hz. The electric current M then has a measurement period corresponding to the measurement frequency of 200 ms. Alternatively, the voltage of the electric current could be any voltage lower than 2 V, preferably between 1 V and 2 V, in particular between 1.1 V and 1.5 V. The measurement frequency could be between 4 Hz and 20 Hz, the measurement period being between 50 ms and 250 ms.

The processing device 23 is then adapted to determine an electrical characteristic representative of the capacity of the tissue of the bone structure 3 between the first 16a and second 17a contact surfaces to conduct electric current M. In particular, based on the voltage of the electric current M, the processing device 23 is adapted to measure the intensity of the electric current M passing through the tissue between the first 16a and second 17a contact surfaces. From the known voltage and the measured intensity of the electric current, the processing device 23 can determine the electrical characteristic, such as electrical resistivity. This measurement of the intensity of the electric current M and the determination of the electrical resistivity may be done on the basis of the frequency measurement, a measurement being carried out at each pulse of the electric current M. Alternatively, the electric generator 22 could deliver an electric current M whose intensity is known and the processing device 23 could be adapted to measure the voltage of the electric current in order to determine the electrical characteristic from the known intensity and the measured voltage of the electric current.

The tissues of the bone structure 3 have different capacities for conducting electric current. For example, cortical bone has a higher electrical resistivity than spongious bone, which in turn has a higher electrical resistivity than fluids such as blood. Such a processing device 23 enables detection of a tissue change in a relative manner, on the basis of a variation in the electrical resistivity, or even the identification of a tissue in an absolute manner, on the basis of an electrical resistivity value.

The processing device 23 is also adapted to emit a warning signal corresponding to the determined electrical resistivity. The warning signal may be one among an audible warning signal, a light warning signal, and a tactile warning signal (vibration), or a combination of such warning signals.

Figure 2:
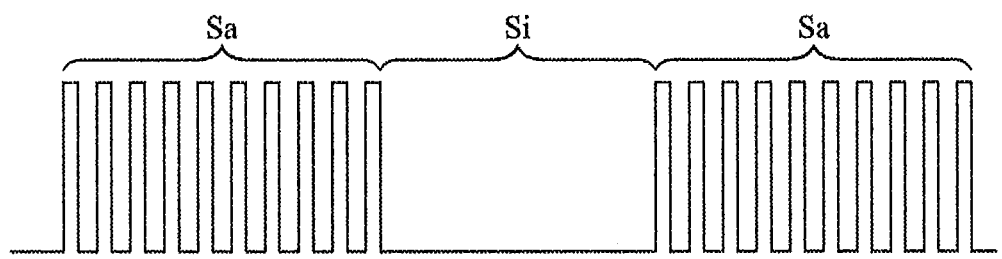
FIG. 2 is a representation of an intermittent warning signal having a warning cadence in which warning sections perceptible to a user are successively emitted with a time interval between two successive warning sections, each warning section having a warning frequency and a warning amplitude.

In FIG. 2, the warning signal, for example audible, is intermittent. It has a warning cadence in which warning sections Sa perceptible to the practitioner are successively emitted with a time interval Si between two successive warning sections Sa. The warning cadence may in particular be between 1 Hz and 20 Hz. The warning cadence is representative of the rate at which the warning sections Sa are issued, for example corresponding to beeps in the case of an audible warning signal. In one particular embodiment, each warning section Sa has a same duration, for example 35.5 ms, the time interval Si corresponding to a time of silence varying in accordance with the warning cadence. A warning period corresponding to the warning cadence and comprising a warning section Sa and a time interval Si is also defined.

In addition, each warning section Sa is periodic and has a warning frequency. The warning frequency may in particular be between 470 Hz and 2600 Hz. The warning frequency is representative of a tone of each of the warning sections Sa, the warning section rising from low to high pitch while increasing the warning frequency. In one particular embodiment, each warning section includes a series of pulses each having a same duration, for example 230 µs.

Each warning section Sa may also have a warning amplitude representative of the intensity at which the warning section Sa is emitted.

Figure 3:
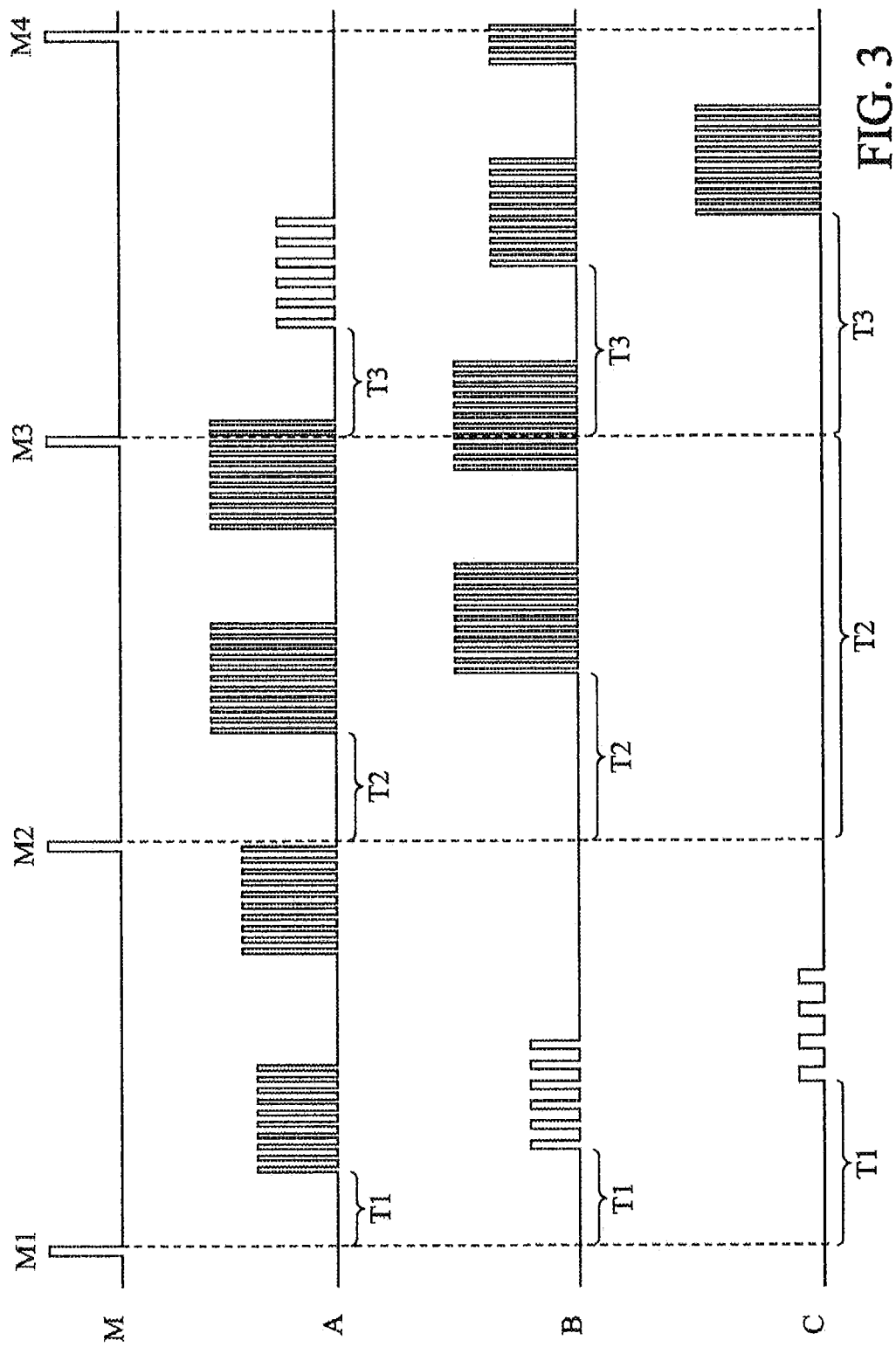
FIG. 3 is a representation of a measurement signal (M) and three warning signals (A, B, C) respectively emitted during the penetration of the medical system into three different anatomical structures, the warning cadence, signal frequency and warning amplitude varying after a time delay following the variation in the electrical characteristic has elapsed.

In the embodiment shown in FIG. 3, the processing device 23 is adapted to vary the set of parameters of the warning signal, namely the warning cadence, the warning frequency, and the warning amplitude, as a function of the electrical resistivity. In particular, the processing device 23:
  increases the warning cadence, the warning frequency, and the warning amplitude of the warning signal when the electrical resistivity decreases, and
  decreases the warning cadence, the warning frequency, and the warning amplitude when the electrical resistivity increases.

Alternatively, the processing device 23 could be adapted to determine an electrical conductivity as an electrical characteristic, and to:
  increase one or more of the parameters selected from among the warning cadence, the warning frequency, and the warning amplitude, when the electrical conductivity increases,
  decrease one or more of the parameters selected from among the warning cadence, the warning frequency, and the warning amplitude, when the electrical conductivity decreases.

Moreover, as is clear from the above, only one or two of the parameters selected from among the warning cadence, warning frequency, and warning amplitude could be variable as a function of the determined electrical characteristic.

Furthermore, as is apparent in FIG. 3, once the variation in the electrical resistivity is detected, the processing device 23 only varies the parameter(s) of the warning signal after a time delay T has elapsed. This time delay can be selected in any manner appropriate for avoiding disruption of the warning signal. It may be fixed or variable.

In FIG. 3, four measurements are performed successively in three different anatomical structures. After the first measurement, a first time delay T1 can be randomly chosen, in particular as a portion of the measurement period. For the subsequent measurements, the time delays correspond to non-elapsed portions of the warning period of the warning signal corresponding to the electrical resistivity determined in the previous measurement.

Thus, during penetration of the body 11 into a first anatomical structure, a first warning signal A is emitted. At a first measurement M1, the processing device 23 determines a first electrical resistivity. After a first random time delay T1, it emits the warning signal with corresponding first warning cadence, warning frequency, and warning amplitude. At a second measurement M2, the processing device 23 determines a second electrical resistivity lower than the first electrical resistivity. After a second time delay T2 substantially corresponding to the time interval of the warning signal of the first measurement, it emits the warning signal with corresponding second warning cadence, warning frequency, and warning amplitude, greater than the first warning cadence, warning frequency, and warning amplitude. At a third measurement M3, the processing device 23 determines a third electrical resistivity greater than the first and second electrical resistivities. After a third time delay T3 corresponding to a portion of the warning period comprising pulses of the warning section and the time interval of the warning signal of the second measurement, it emits the warning signal with corresponding third warning cadence, warning frequency, and warning amplitude, which are less than the first and second warning cadence, warning frequency, and warning amplitude.

Similarly, during penetration of the body 11 into a second anatomical structure, a second warning signal B is emitted. At the first measurement M1, the processing device 23 determines a first electrical resistivity. After a first random time delay T1, it emits the warning signal with corresponding first warning cadence, warning frequency, and warning amplitude. At the second measurement M2, the processing device 23 determines a second electrical resistivity lower than the first electrical resistivity. After a second time delay T2 corresponding to a portion of the time interval of the warning signal of the first measurement, it emits the warning signal with corresponding second warning cadence, warning frequency, and warning amplitude, greater than the first warning cadence, warning frequency, and warning amplitude. At the third measurement M3, the processing device 23 determines a third electrical resistivity lower than the first electrical resistivity and greater than the second electrical resistivity. After a third time delay T3 corresponding substantially to a portion of the warning period comprising pulses of the warning section and the time interval of the warning signal of the second measurement, it emits the warning signal with corresponding third warning cadence, warning frequency, and warning amplitude, which are greater than the first warning cadence, warning frequency, and warning amplitude, and less than the second warning cadence, warning frequency, and warning amplitude.

During penetration of the body 11 into a third anatomical structure, a third warning signal C is emitted. At the first measurement M1, the processing device 23 determines a first electrical resistivity. After a first random time delay T1, it emits the warning signal with corresponding first warning cadence, warning frequency, and warning amplitude. At the second measurement M2, the processing device 23 determines a second electrical resistivity. However, this measurement occurs during a second time delay corresponding to a portion of the time interval of the first measurement. No warning signal corresponding to the second measurement is emitted before the third measurement M3 is carried out. At the third measurement M3, the processing device 23 determines a third electrical resistivity lower than the first electrical resistivity. After a third time delay T3 corresponding to a portion of the time interval of the first measurement, it emits the warning signal with corresponding second warning cadence, warning frequency, and warning amplitude, which are greater than the first warning cadence, warning frequency, and warning amplitude.

Alternatively, the time delay T could be selected in any other suitable manner. The time delay may in particular be between 30% and 100% of the time interval Si, in particular between 50% and 100% of the time interval Si, and for example between 60% and 90% of the time interval Si.

According to another variant, the time delay may be equal to at least a portion of the measurement period, preferably between 10% and 500% of the measurement period. In this other variant, when the time delay is greater than twice the measurement period, the processing device may be adapted to calculate an average electrical characteristic from the electrical characteristics determined in each of the measurement periods occurring during the time delay. The parameter(s) of the warning signal can then be adjusted on the basis of the calculated average electrical characteristic. These provisions limit the sensitivity of the surgical instrument 10 to local inhomogeneities.

In relation to FIGS. 4-7, use of the surgical instrument 10 during formation of a hole in one of the vertebral pedicles is described. Cortical bone has an electrical resistivity greater than that of spongious bone, and spongious bone has an electrical resistivity greater than that of blood.

Figure 4:
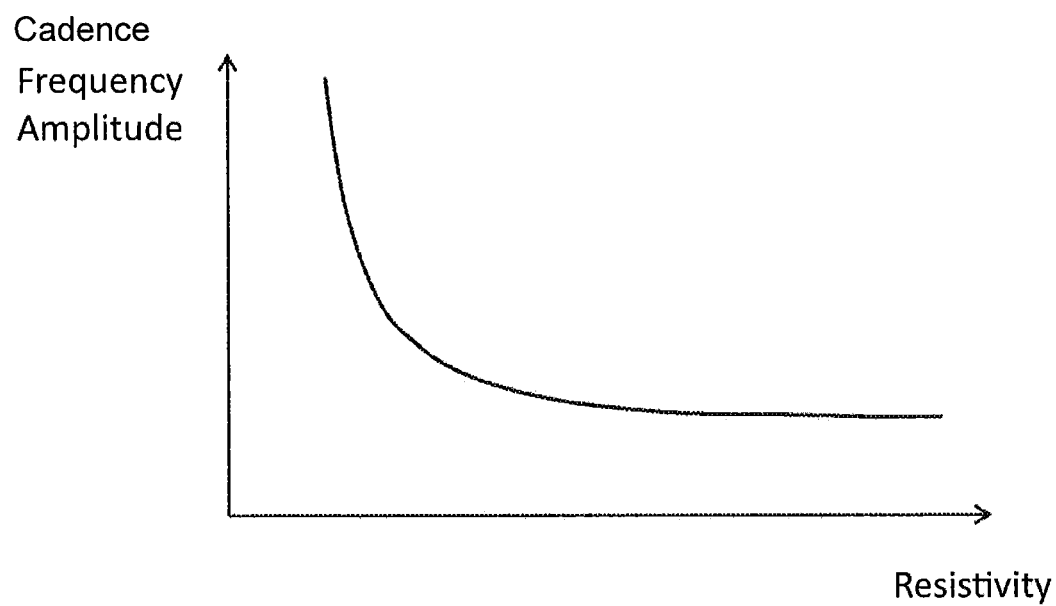
FIG. 4 is a representation of a transfer function stored in the processing device and associating a value of a warning cadence, warning frequency, and/or warning amplitude with each of the values of the electrical characteristic.

FIG. 4 shows an example transfer function stored in the processing device 23 and associating a value for the warning cadence, warning frequency, and/or warning amplitude for each value of the electrical resistivity. When the tissue with which the first 16a and second 17a contact surfaces of the surgical instrument 10 are in contact changes, a variation in the electrical resistivity occurs which results in a variation of at least one of the parameters among the warning cadence, warning frequency, and warning amplitude.

The transfer function is chosen so as to reduce the warning cadence, warning frequency, and/or warning amplitude as the electrical resistivity increases.

In this manner, when the first 16a and second 17a contact surfaces of the surgical instrument 10 are in contact with blood or soft tissue which have low electrical resistivity, the warning signal has a high warning cadence, warning frequency, and warning amplitude. When the first 16a and second 17a contact surfaces of the surgical instrument 10 are in contact with spongious bone which has electrical resistivity between that of blood or soft tissue and cortical bone, the warning signal has an intermediate warning cadence, warning frequency, and warning amplitude. And when the first 16a and second 17a contact surfaces of the surgical instrument 10 are in contact with cortical bone which has high electrical resistivity, the warning signal has a low warning cadence, warning frequency, and/or warning amplitude.

The transfer function is also selected so that it varies the warning cadence, warning frequency, and/or warning amplitude more significantly for low electrical resistivities than for high electrical resistivities.

In this manner, the surgical instrument interprets variations in electrical resistivity with more sensitivity in situations presenting the greatest risk to the patient, meaning when the first 16a and second 17a contact surfaces of the surgical instrument 10 are in contact with or in proximity to blood or soft tissue.

Figure 5:
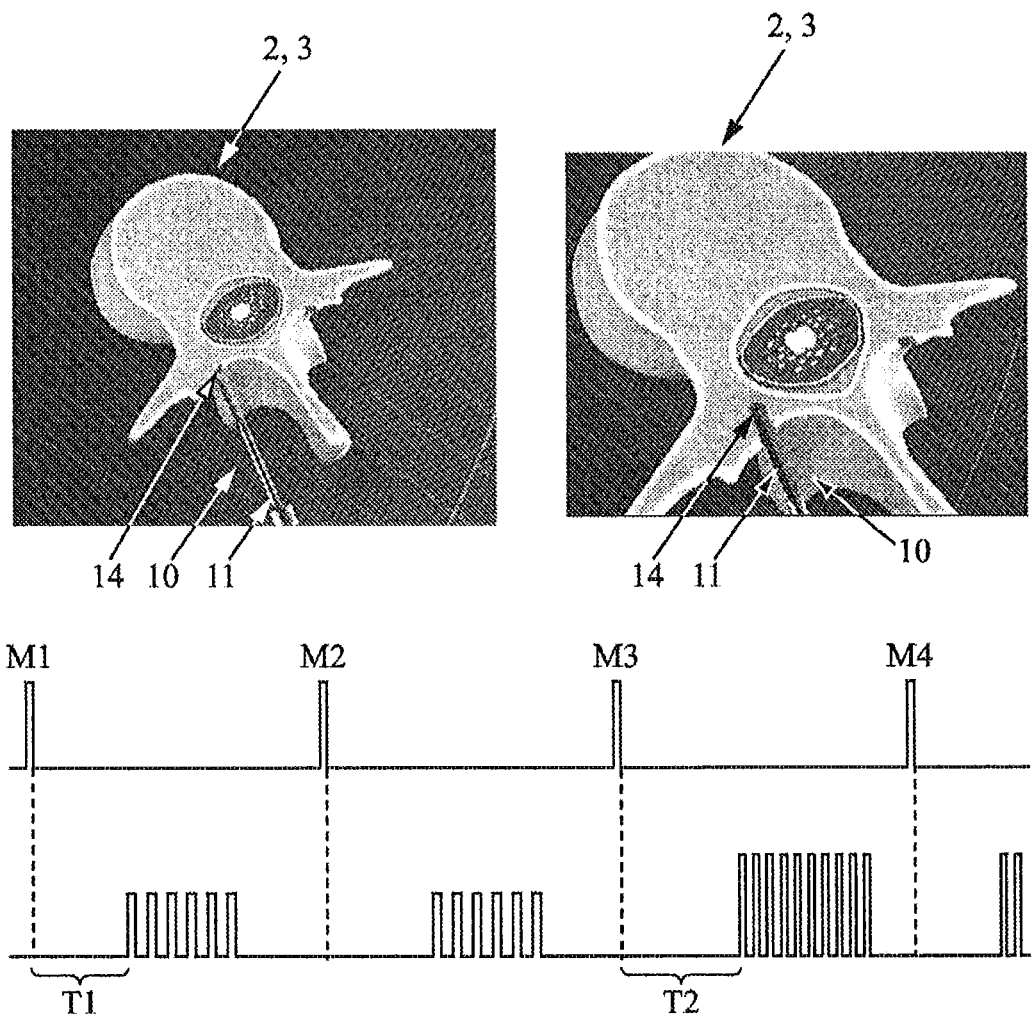
FIGS. 5, 6, and 7 are representations of the measurement signal and warning signal during penetration of the medical system into a vertebra of the spinal column of a patient.

In FIG. 5, two first measurements M1, M2 are made while the distal end 14 of the body 11 of the surgical instrument 10, carrying the first 16a and second 17a contact surfaces, is in contact with the outer layer of cortical bone. After a first time delay T1 following the first measurement M1, the first warning signal corresponding to the electrical resistivity of the cortical bone is emitted and continues to be emitted after the second measurement M2, no variation of the electrical resistivity having been detected. At the third measurement M3, the distal end 14 of the body 11 of the surgical instrument 10 has penetrated spongious bone. After a second delay time T2 after the third measurement M3, the second warning signal corresponding to the electrical resistivity of spongious bone is emitted and continues to be emitted after the fourth measurement M4, as no change in the electrical resistivity has been detected.

Figure 6:
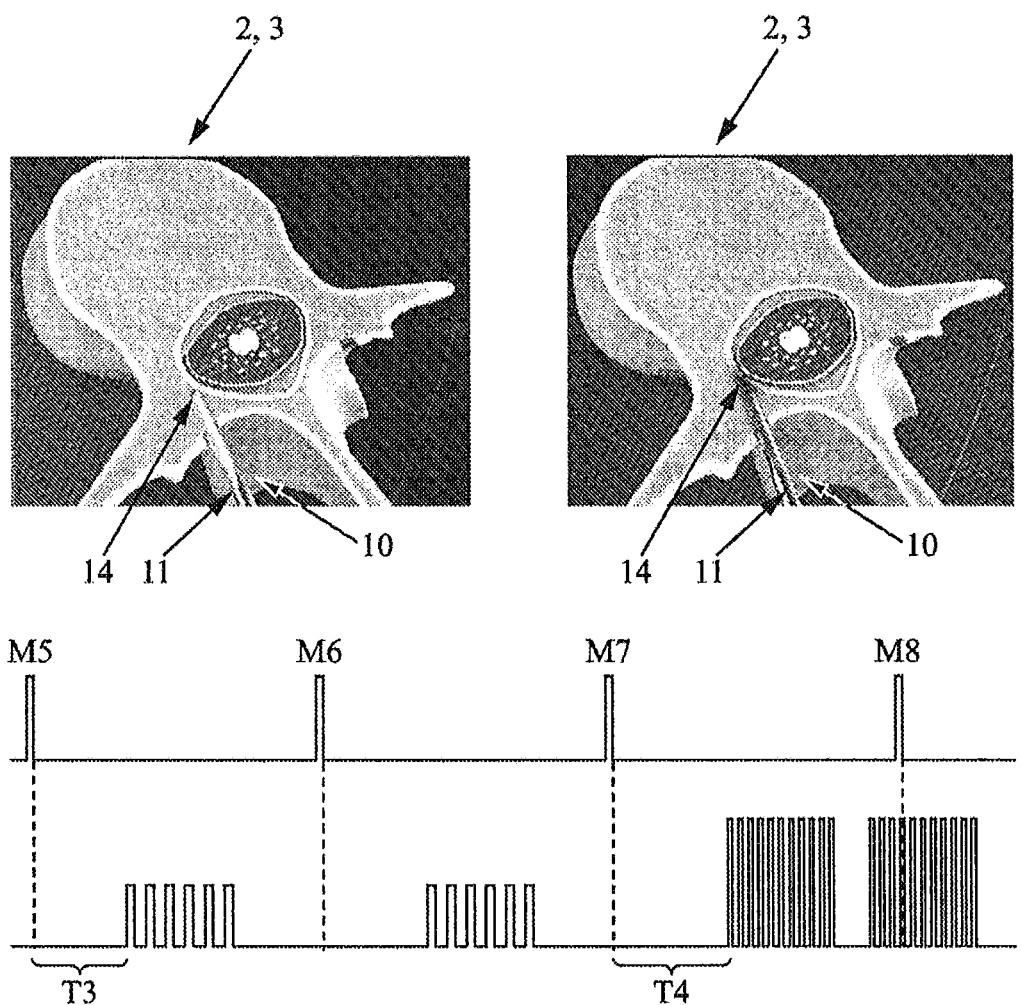

In FIG. 6, at the fifth measurement M5, the distal end 14 of the body 11 of the surgical instrument 10 is near the internal layer of cortical bone bordering the vertebral foramen. After the third time delay T3 following the fifth measurement M5, the first warning signal corresponding to the electrical resistivity of cortical bone is emitted and continues to be emitted after the sixth measurement M6, as no change in the electrical resistivity has been detected. At the seventh measurement M7, the distal end 14 of the body 11 of the surgical instrument 10 has breached the cortical bone so that blood seeps into the cavity formed by the body 11. After a fourth time delay T4 following the seventh measurement M7, the third warning signal corresponding to the electrical resistivity of blood is emitted and continues to be emitted after the eighth measurement M8, as no change in the electrical resistivity has been detected.

Figure 7:
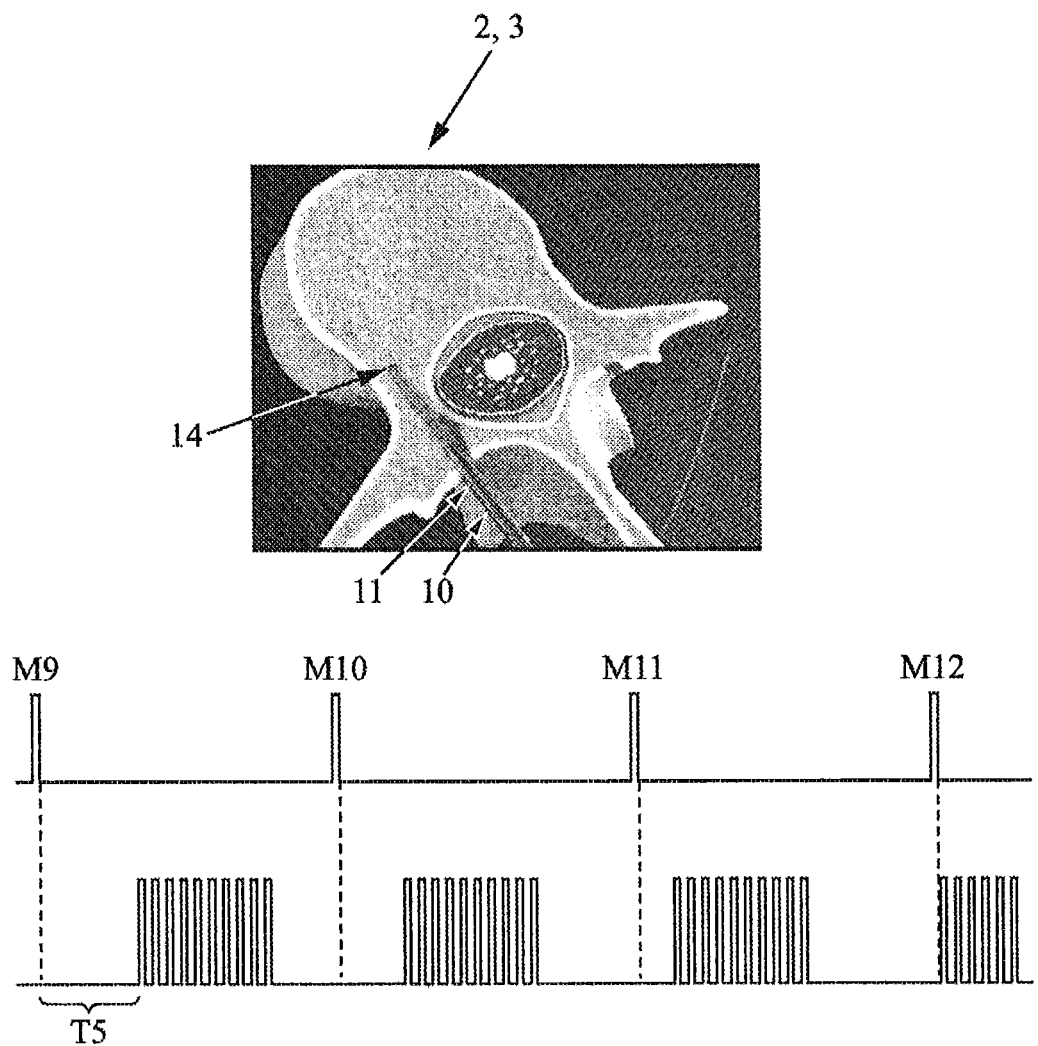

In FIG. 7, before the ninth measurement M9, the practitioner has corrected the path after perceiving the third warning signal. The distal end 14 of the body 11 of the surgical instrument 10 has been returned to the spongious bone so that after a fifth time delay T5 following the ninth measurement M9, the second warning signal corresponding to the electrical resistivity of spongious bone is emitted and continues to be emitted after the tenth M10, eleventh M11, and twelfth M12 measurements, as no change in the electrical resistivity has been detected.

Alternatively, to limit the sensitivity of the surgical instrument to local inhomogeneities, electrical resistivity ranges can be defined based on thresholds. Corresponding parameters of the warning signal can be selected for each electrical resistivity range. The parameter(s) of the warning signal then remain constant as long as the determined electrical resistivity is within a certain range, below a certain threshold. When the determined electrical resistivity changes electrical resistivity range and exceeds the threshold concerned, one or more parameters selected from among the warning cadence, warning frequency, and warning amplitude may vary.

In particular, with a surgical instrument similar to the surgical instrument described above but for determining an absolute value of the electrical resistivity instead of a simple variation in the electrical resistivity, three electrical resistivity ranges could be defined. One could thus define:

a first electrical resistivity range for cortical bone with which is associated a first warning signal with low and constant warning cadence, warning frequency, and warning amplitude, a second electrical resistivity range for spongious bone with which is associated a second warning signal with intermediate and constant warning cadence, warning frequency, and warning amplitude, a third electrical resistivity range for blood or soft tissue with which is associated a third warning signal with high and constant warning cadence, warning frequency, and warning amplitude.

The invention claimed is:

1. A medical system intended for penetrating an anatomical structure of a patient, the anatomical structure having tissues presenting different capacities for conducting electric current, said medical system comprising:
   a body suitable for penetrating the anatomical structure, the body having an outer surface,
   at least one first electrode having a first contact surface arranged on the outer surface of the body so as to come into contact with the tissues of the anatomical structure,
   at least one second electrode having a second contact surface arranged on the outer surface of the body so as to come into contact with the tissues of the anatomical structure at a distance from the first contact surface,
   an electric generator suitable for applying an electric current between the first and second contact surfaces,
   a processing device suitable for determining an electrical characteristic representative of the capacity of the tissue of the anatomical structure between the first and second contact surfaces to conduct the electric current, and for emitting a warning signal corresponding to the determined electrical characteristic, the warning signal having at least one parameter that varies as a function of the determined electrical characteristic,
   wherein the warning signal is intermittent and has a plurality of different warning cadences as the parameter that varies as a function of the determined electrical characteristic, each of the warning cadences being composed of successive warning periods each composed of one user-perceptible warning section followed by one time interval, the warning sections of the warning periods of different warning cadences having a same duration and the time intervals of the warning periods of different warning cadences having different durations,
   wherein the processing device is suitable for:
   as the warning signal is emitted with a first warning cadence having a first warning period and corresponding to a first electrical characteristic, performing a detection of an electrical characteristic variation from the first electrical characteristic to a second electrical characteristic, the detection of the electrical characteristic variation occurring during one of the first warning period,
   determining a second warning cadence having a second warning period corresponding to the second electrical characteristic, and
   after a time delay equal to a remaining portion of the first warning period following the detection of the electrical characteristic variation has elapsed so as to allow the warning signal to complete the first warning period, emitting the warning signal with the second warning cadence.

2. The medical system according to claim 1, wherein at least one of the warning cadences is between 1 Hz and 20 Hz.

3. The medical system according to claim 1, wherein the warning signal has a plurality of different warning frequencies at which each of the warning sections is emitted as a second parameter that varies as a function of the determined electrical characteristic, the plurality of different warning frequencies including a first warning frequency and a second warning frequency, the processing device adapted to modify the first warning frequency of the warning signal to the second warning frequency after the time delay has elapsed.

4. The medical system according to claim 3, wherein at least one of the plurality of the warning frequencies is between 470 Hz and 2600 Hz.

5. The medical system according to claim 1, wherein the warning signal has a plurality of different warning amplitudes as a second parameter that varies as a function of the determined electrical characteristic, the plurality of different warning amplitudes including a first warning amplitude and a second warning amplitude, the processing device adapted to modify the first warning amplitude of the warning signal to the second warning amplitude after the time delay has elapsed.

6. The medical system according to claim 1, wherein the processing device is adapted to determine an electrical conductivity as the first and second electrical characteristics, and to:
  increase the warning signal parameter when the electrical conductivity increases,
  decrease the warning signal parameter when the electrical conductivity decreases.

7. The medical system according to claim 1, wherein the processing device is adapted to determine an electrical resistivity as the first and second electrical characteristics, and to:
  increase the warning signal parameter when the electrical resistivity decreases,
  decrease the parameter of the warning signal when the electrical resistivity increases.

8. The medical system according to claim 1, wherein the processing device is adapted to keep constant said at least one variable parameter of the warning signal as long as the electrical characteristic is below a threshold, and to vary the parameter of the warning signal when the electrical characteristic reaches the threshold.

9. Method for implementing a medical system for penetrating an anatomical structure of a patient, the anatomical structure having tissues presenting different capacities for conducting electric current, the medical system comprising:
  a body configured to penetrate the anatomical structure, the body having an outer surface,
  at least one first electrode having a first contact surface arranged on the outer surface of the body so as to come into contact with the tissues of the anatomical structure,
  at least one second electrode having a second contact surface arranged on the outer surface of the body so as to come into contact with the tissues of the anatomical structure at a distance from the first contact surface,
  an electric generator configured to apply an electric current between the first and second contact surfaces, and
  a processing device configured to:
    determine an electrical characteristic representative of the capacity of the tissue of the anatomical structure between the first and second contact surfaces to conduct the electric current, and emit a warning signal corresponding to the determined electrical characteristic, the warning signal having at least one parameter that varies as a function of the determined electrical characteristic, wherein the warning signal is intermittent and has a plurality of different warning cadences as the parameter that varies as a function of the determined electrical characteristic, each of the warning cadences being composed of successive warning periods each composed of one user-perceptible warning section followed by one time interval, the warning sections of the warning periods of different warning cadences having a same duration and the time intervals of the warning periods of different warning cadences having different durations,
    as the warning signal is emitted with a first warning cadence having a first warning period and corresponding to a first electrical characteristic, perform a detection of an electrical characteristic variation from the first electrical characteristic to a second electrical characteristic, the detection of the electrical characteristic variation occurring during the first warning period,
    determine a second warning cadence having a second warning period corresponding to the second electrical characteristic, and
    after a time delay equal to a remaining portion of the first warning period following the detection of the electrical characteristic variation has elapsed so as to allow the warning signal to complete the first warning period, emit the warning signal with the second warning cadence, the method for implementing comprising:
  penetrating the anatomical structure with the body of the medical system, the first contact surface of the first electrode arranged on the outer surface of the body coming into contact with the tissues of the anatomical structure, and the second contact surface of the second electrode arranged on the outer surface of the body coming into contact with the tissues of the anatomical structure at the distance from the first contact surface,
  applying the electric current between the first and second contact surfaces,
  determining the electrical characteristic representative of the capacity of the tissue of the anatomical structure between the first and second contact surfaces to conduct the electric current, and
  emitting the warning signal corresponding to the determined electrical characteristic,
  as the warning signal is emitted with the first warning cadence having the first warning period and corresponding to the first electrical characteristic, performing the detection of the electrical characteristic variation from the first electrical characteristic to the second electrical characteristic, the detection of the electrical characteristic variation occurring during the first warning period,
  determining the second warning cadence having the second warning period corresponding to the second electrical characteristic, and
  after the time delay equal to the remaining portion of the first warning period following the detection of the electrical characteristic variation has elapsed so as to allow the warning signal to complete the first warning period, emitting the warning signal with the second warning cadence.

10. The method according to claim 9, wherein at least one of the warning cadences is between 1 Hz and 20 Hz.

11. The method according to claim 9, wherein the warning signal has a plurality of different warning frequencies at which each of the warning sections is emitted as a second parameter that varies as a function of the determined electrical characteristic, the plurality of different warning frequencies including a first warning frequency and a second warning frequency, the processing device adapted to modify the first warning frequency of the warning signal to the second warning frequency after the time delay has elapsed.

12. The method according to claim 11, wherein at least one of the warning frequencies is between 470 Hz and 2600 Hz.

13. The method according to claim 9, the warning signal has a plurality of warning amplitudes as a second parameter that varies as a function of the determined electrical characteristic, the plurality of warning amplitudes including a first warning amplitude and a second warning amplitude, the processing device adapted to modify the first warning amplitude of the warning signal to the second warning amplitude after the time delay has elapsed.

14. The method according to claim 9, comprising determining an electrical conductivity as the first and second electrical characteristics, and:
increasing the warning signal parameter when the electrical conductivity increases,
decreasing the warning signal parameter when the electrical conductivity decreases.

15. The method according to claim 9, comprising determining an electrical resistivity as the first and second electrical characteristics, and:
increasing the warning signal parameter when the electrical resistivity decreases,
decreasing the parameter of the warning signal when the electrical resistivity increases.

16. The method according to claim 1, comprising keeping constant said at least one variable parameter of the warning signal as long as the electrical characteristic is below a threshold, and varying the parameter of the warning signal when the electrical characteristic reaches the threshold.

* * * * *